(12) United States Patent
Spagnol et al.

(10) Patent No.: US 6,632,969 B1
(45) Date of Patent: Oct. 14, 2003

(54) METHOD FOR SEPARATING A DIPHOSPHINE DIASTEREOISOMERS

(75) Inventors: Michel Spagnol, Meyzieu (FR); Francois Mathey, Paris (FR); Francois Mercier, Versailles (FR); Frederic Robin, Montrouge (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/646,390

(22) PCT Filed: Mar. 15, 1999

(86) PCT No.: PCT/FR99/00570

§ 371 (c)(1),
(2), (4) Date: Jan. 12, 2001

(87) PCT Pub. No.: WO99/47475

PCT Pub. Date: Sep. 23, 1999

(30) Foreign Application Priority Data

Mar. 16, 1998 (FR) .............................................. 98 03182

(51) Int. Cl.[7] .................................................. C07F 9/02
(52) U.S. Cl. ........................................ 568/12; 556/12
(58) Field of Search .............................. 556/18, 13, 16; 568/12

(56) References Cited

U.S. PATENT DOCUMENTS 5,783,738 A * 7/1998 Mathey et al. ................. 568/12
6,288,279 B1 * 9/2001 Mathey et al. ................. 568/12

FOREIGN PATENT DOCUMENTS

| WO | 96 20202 | 7/1996 |
| WO | 98 39345 | 9/1998 |

OTHER PUBLICATIONS

CA:129:245293 abs of WO 9839345 Mar. 1998.*
CA: 117:48704 abs by Bevierre et al Bull Soc Chim Fr. 129(1) pp 1–8 1992.*
CA:127:331575 abs by Robin et al Chem Eur J 3(8) pp 1365–1369 1997.*
Bevierre M.O. et al, "Mechanism of the thermal tetramerization of phospholes", Bull. Soc. Chim. Fr. (BSCFAS, 00378968); 92; vol. 129 (1); pp. 1–8, XP002083579 Ec. Polytech.; Lab. Chim. Phosphore Met. Transition; Palaiseau; 91128; Fr. (FR) cited in the application, see the whole document (1992).

* cited by examiner

Primary Examiner—Jean F. Vollano
(74) Attorney, Agent, or Firm—Burns, Doane, Swecker & Mathis, L.L.P.

(57) ABSTRACT

A process for separating the (d/l) and (meso) diastereoisomers of bis-[1-phospha-2,3-diphenyl-4,5-dimethylnorbornadiene] comprising converting the mixture of diastereoisomers of bis-[1-phospha-2,3-diphenyl-4,5-dimethylnorbornadiene] to a mixture of the corresponding diastereoisomers of diphosphine disulphide or dioxide, then in separating the two diastereoisomers in dioxide or disulphide form.

26 Claims, No Drawings

METHOD FOR SEPARATING A DIPHOSPHINE DIASTEREOISOMERS

This application is the national phase of PCT/FR99/00570, filed Mar. 15, 1999 now WO99/47475

The present invention relates to a process for separating the (d/l) and (meso) diastereoisomers of bis-[1-phospha-2,3-diphenyl-4,5-dimethyinorbornadiene].

The invention also relates to a preparation process for optically active diphosphines of bis-[1-phospha-2,3-diphenyl-4,5-dimethylnorbornadiene].

The preparation of a mixture of diasteroisomers of bis-[1-phospha-2,3-diphenyl-4,5-dimethylnorbornadiene] has been described by F. Mathey et al, in Bull. Soc. Chim. Fr. 129, pp. 1–8 (1992).

The starting product of the synthesis of this is 1-phenyl-3,4-dimethylphosphole (II) described by F. Mathey et al, in Synthesis, 1993, pp.983.

The operation starts by preparing 3,3',4,4'-tetrarethyl-1,1'-diphosphole-(IV). To that end 1-phenyl-3,4-dimethylphosphole (II) in THF is reacted with lithium metal according to the following reaction:

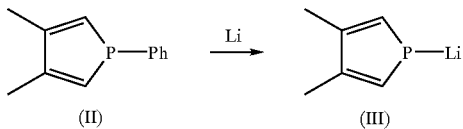

At the end of the reaction aluminium chloride is introduced to trap the phenyllithium produced during the reaction.

In a following stage, the dimerization of (II) is carried out by the action of diiodine $I_2$ in THF. For further details on the preparation of (IV) the article by F. Mathey et al, Organometallics, 1983, 2, 1234 can be referred to.

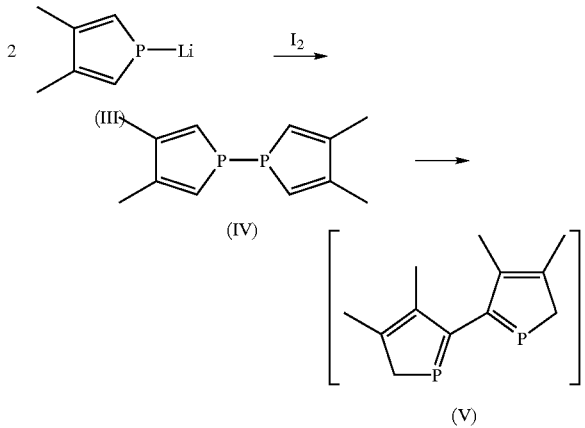

By heating at about 140° C., compound (IV) rearranges to (V) which reacts with diphenylacetylene according to Diels-Adler, in order to produce bis-[1-phospha-2,3-diphenyl-4,5-dimethylnorbornadiene].

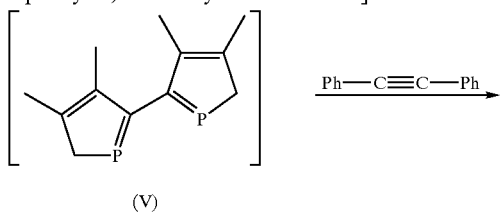

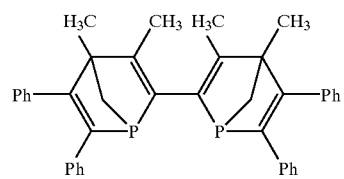

A practical embodiment is given on page 6 of the publication by F. Mathey et al, in Bull. Soc. Chim. Fr. 129, pp. 1–8 (1992).

However, as mentioned on page 3, right-hand column, lines 7 and 8, the authors obtained a mixture of two diastereoisomers, subsequently identified by the Applicant as being a meso (Im)—RS,SR—and a racemic (Ir)—RR,SS—called (13b) and (13a) respectively in the article.

The publication mentions the separation of the two diastereoisomers by the formation of a palladium (II) chelateo. In order to do this, the separation of the mixture of diastereoisomers obtained is described, by reaction with $PdCl_2(PhCN)_2$ in dichloroethane leading to (VIm) and (VIr), separation by chromatography on silica gel followed by elution, then decomplexation carried out with NaCN.

Therefore, the two diastereoisomers are recovered separately, on the one hand meso (Im) and on the other hand the racemic (Ir).

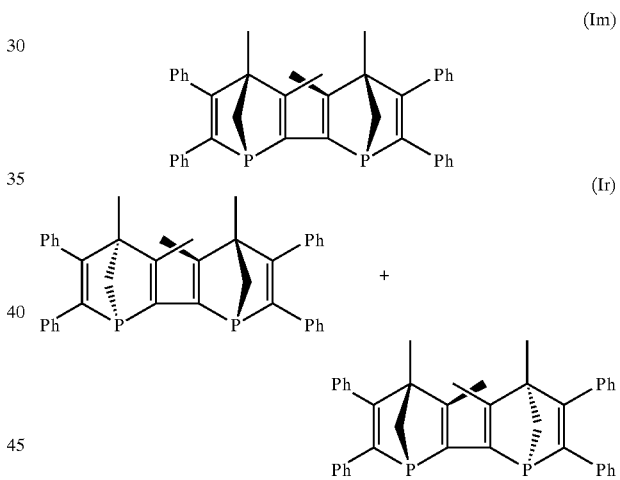

The process described above allows separation of the diastereoisomers but it is currently difficult to use on an industrial scale as the palladium complex is expensive.

The purpose of the present invention is to make available a more economical process for the separation of the diastereoisomers.

It has been found that the (d/l) and (meso) diastereoisomers of bis-[1-phospha-2,3-diphenyl-4,5-dimethyinorbomadiene] can be separated according to a process which consists of converting the mixture of diastereoisomers of bis-[1-phospha-2,3-diphenyl-4,5-dimethylnorbornadiene] to a mixture of diastereoisomers of the corresponding diphosphine dioxide or disulphide, then separating the two diastereoisomers in the form of the dioxide or disulphide.

According to a first variant of the invention, the separation of the diastereoisomers of the bis-[1-phospha-2,3-diphenyl-4,5-dimethylnorbomadiene]dioxide obtained is carried out by subjecting the mixture of diastereoisomers of bis-[1-phospha-2,3diphenyl-4,5-dimethylnorbornadiene] to an oxidation reaction thus convert them to bis-[1-phospha-2,3-diphenyl-4,5-dimethylnorbornadiene]dioxide.

Another variant of the invention consists of carrying out the separation of the diastereoisomers of the bis-[1-phospha-2,3-diphenyl-4,5-dimethylnorbornadiene]dioxide obtained by reacting the mixture of diastereoisomers of bis-[1-phospha-2,3-diphenyl-4,5-dimethylnorbornadiene] with sulphur leading to a mixture of diastereoisomers of the bis-[1-phospha-2,3-diphenyl-4,5-dimethylnorbornadiene] disulphide.

Dioxides of Diphosphines in Meso or Racemic Form

Another object of the invention is the dioxides of bis-[1-phospha-2,3-diphenyl-4,5-dimethylnorbornadiene] in meso or racemic form as well as the process for obtaining them.

According to a first operation, the diastereoisomers are converted into oxide form.

They can be symbolized by the following formula:

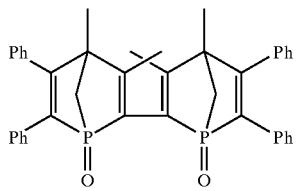

(IX)

The oxides of diphosphines of formula (IX) are obtained by oxidation of the two diastereoisomers of formula (Im) amd (Ir) using an oxidizing agent.

Although any type of oxidizing agent can be used, a chemical oxidizing agent, for example potassium permanganate or molecular oxygen or a gas containing it, it is preferable to use hydrogen peroxide, preferably, in the form of an aqueous solution.

The concentration of the hydrogen peroxide solution is advantageously comprised between 10% and 35% by weight.

The quantity of oxidizing agent used can vary widely from the stoichiometric quantity up to an excess representing for example 20 times the stoichiometry.

An organic solvent can be used which solubilizes all the reagents. The solvent can be chosen from aliphatic, cyclo aliphatic or aromatic hydrocarbons, preferably aromatic hydrocarbons. Examples are given below.

Among all these solvents, toluene and the xylenes are preferred.

The concentration of diphosphine in the reaction solvent is preferably between 0.05 and 1 mole/litre and yet more particularly between 0.05 and 0.2 mole/litre.

Thus the diastereoisomers which are generally dissolved in a suitable solvent are brought into contact with the oxidizing agent.

The reaction is advantageously carried out between 50° C. and 100° C.

The duration of the reaction is generally between 30 minutes and 4 hours.

The oxides of diphosphine are recovered from the organic phase.

The aqueous and organic phases are separated.

A standard treatment of the phases is carried out.

Thus the aqueous phase is washed several times (from 1 to 3) with an organic solvent for extraction of the diphosphine oxides, for example ethyl ether.

All the organic phases are collected and they are washed with salt water (saturated solution of sodium chloride) then a usual drying operation is preferably carried out, over a desiccating agent for example sodium or magnesium sulphate.

In a following stage, the oxides of the two diastereoisomers are separated.

The solvent is concentrated by evaporation, then the separation is carried out in a known manner [A. Bertheillier—Dunod Paris (1972)] by liquid chromatography on a column, preferably with a silica support.

The column is eluted with a mixture of suitable solvents.

The solvents suitable for the separation are determined, by simple execution operations for a person skilled in the art which consist of carrying out a chromatography on a silica plate.

The solvents are generally chosen from ethyl acetate, methanol, ethyl ether or their mixtures.

Therefore, depending on the case, the diphosphine dioxide is meso form (IXm) and the diphosphine dioxide in racemic form (IXr) are recovered in a variable order, in the elution solvents.

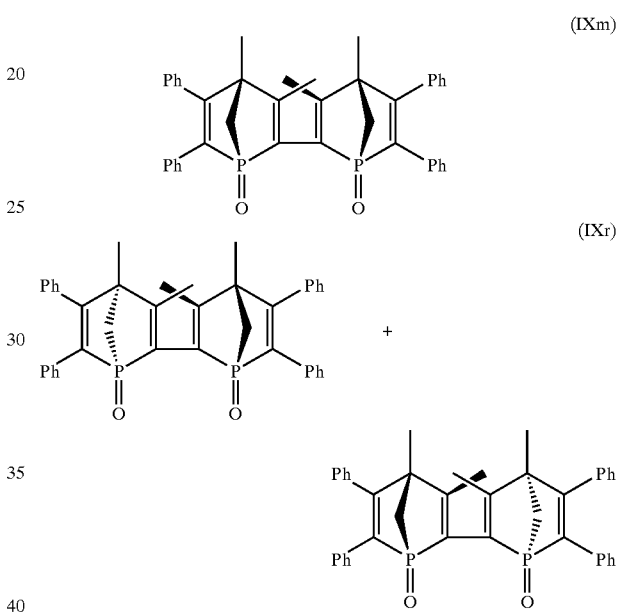

Disulphides of Diphosphines in Recemic or Meso Form

Another object of the invention is the disulphides of bis-[1-phospha-2,3-diphenyl-4,5-dimethylnorbornadiene] in meso or racemic form as well as the process for obtaining them.

It has also been found that the diastereoisomers can be separated according to a process which consists of reacting the mixture of diastereoisomers (Im) and (Ir) with sulphur, thus converting them to diphosphine disulphide (IX'm) and (IX'r), then separating the two diastereoisomers of the diphosphine disulphides.

According to a first operation, the diastereoisomers are converted into sulphide form.

They can be symbolized by the following formula:

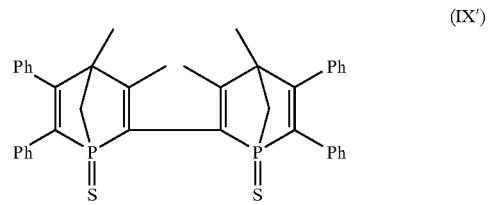

(IX')

Therefore, sulphur ($S_8$) is reacted with the mixture of the two diastereoisomers in meso form (Im) and in racemic form (Ir) leading to a mixture of the disulphides of diphosphines, in meso or racemic form.

Generally, the quantity of sulphur used defined relative to each phosphorus atom varies from the stoichiometric quantity up to a slight excess of 10%.

The reaction takes place at a temperature ranging from ambient temperature to about 100° C., preferably, around 80° C., in a solvent of aromatic hydrocarbon type, and in particular toluene.

In a following stage, the mixture of diastereoisomers is separated on a silica column as described previously.

Thus, diphosphine disulphide in meso form (IX'm) and diphosphine disulphide in racemic form (IX'r) are recovered:

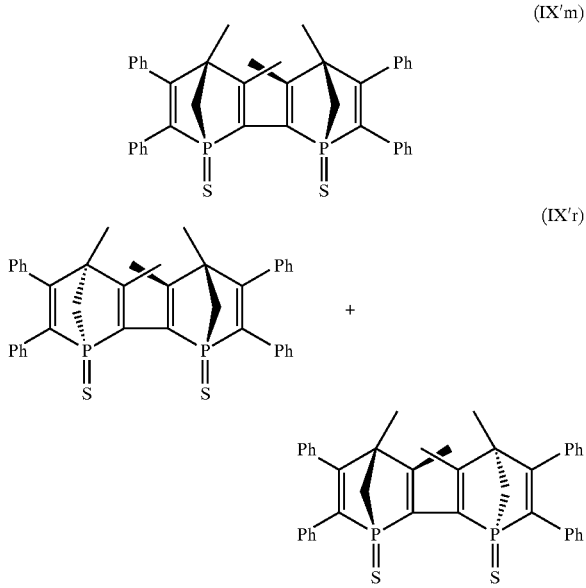

Diphosphines in Enantiomeric Form

Another object of the present invention is the preparation process for the optically active diphosphines of bis-[1-phospha-2,3-diphenyl-4,5-dimethylnorbornadiene] corresponding to the following formulae:

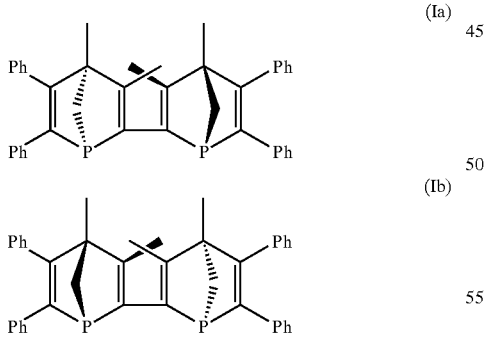

The invention therefore provides a preparation process for diphosphines, chiral on the phosphorous and non racemisable.

A first variant for obtaining an optically active diphosphine of formula (Ia) or (Ib) consists of carrying out the resolution of bis-[1-phospha-2,3-diphenyl-4,5-dimethyinorbomadiene]dioxide in racemic form (IXr), then separately carrying out the reduction of the enantiomers of bis-[1-phospha-2,3-diphenyl-4,5-dimethyinorbornadiene] dioxide obtained (IXa) or (IXb).

Another variant of the invention consists of firstly carrying out the reduction of bis-[1-phospha-2,3-diphenyl-4,5-dimethylnorbornadiene]dioxide in racemic form (IXr) to bis-[1-phospha-2,3-diphenyl-4,5-dimethylnorbornadiene] in racemic form (Ir), then carrying out the resolution of bis-[1-phospha-2,3-diphenyl-4,5-dimethylnorbornadiene] in racemic form (Ir) to enantiomers (Ia) and (Ib).

Another variant of the invention consists of carrying out the resolution of the racemic mixture of bis-[1-phospha-2,3-diphenyl-4,5-dimethylnorbornadiene]disulphide (IX'r) then reducing the enantiomers of bis-[1-phospha-2,3-diphenyl-4,5-dimethylnorbornadiene]disulphide (IX'a) and (IX'b) to the enantiomers of bis-[1-phospha-2,3-diphenyl-4,5-dimethylnorbornadiene] (Ia) and (Ib).

Another variant consists of reducing the racemric mixture of bis-[1-phospha-2,3-diphenyl-4,5-dimethylnorbornadiene]disulphide (IX'r) to the racemic mixture of bis-[1-phospha-2,3-diphenyl-4,5-dimethylnorbornadiene] (Ir) then carrying out the resolution of the racemic mixture of bis-[1-phospha-2,3-diphenyl-4,5-dimethyinorbornadiene] to enantiomers (Ia) and (Ib).

Another variant of the invention is the conversion of the racemic mixture of bis-[1-phospha-2,3-diphenyl-4,5-dimethylnorbornadiene]disulphide (IX'r) to the racemic mixture of bis-[1-phospha-2,3-diphenyl-4,5-dimethylnorbornadiene]dioxide (IXr) and then obtaining the optically active diphosphines (Ia) and (Ib) according to the methods described previously.

Enantiomers Oxide Route

According to a first embodiment of the invention, the resolution of the racemic mixture of bis-[1-phospha-2,3-diphenyl-4,5-dimethylnorbornadiene]dioxide (IXr) is carried out.

The resolution can be carried out by separation of the two enantiomers, by chiral liquid chromatography. A chiral column is used, for example, Chiralcel OJ® [column of modified cellulose ester (cf. ref mentioned hereafter p.262)., Chirose C1 or C3® (cross-linked polymer bonded on silica), Chirosebond C1 or C3® (graft of chiral polymer of polyholoside type on spherical silica 5 µm–100 Å) and the elution solvents can be in particular a water/acetonitrile mixture.

The implementation of the separation is carried out according to standard techniques of the fields considered (cf. Stereochimie des composes chimiques Ernest L. Eliel et al Technique et Documentation 1996, p. 249–250).

In this way, two enantiomers are obtained:

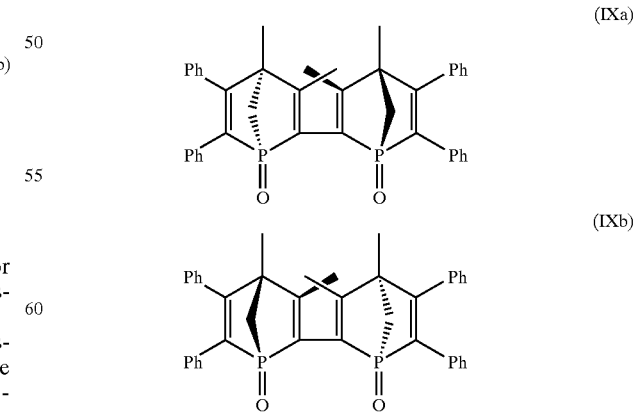

In a following stage, the optically active dioxides of bis-[1-phospha-2,3-diphienyl-4,5-dimethylnorbornadiene]

of formula (IXa) or (IXb) are reduced. Reference can be made to the description of the reduction operation given hereafter.

Another variant consists of firstly carrying out the reduction of bis-[1-phospha-2,3-diphenyl-4,5-dimethylnorbornadiene]dioxide in racemic form then carrying out the resolution of the diphosphine in racemic form obtained.

The reduction can be carried out with a reducing agent such as for example trichlorosilane, hexachlorodisilazane, phenyltrisilane, a hydride in particular $LiAlH_4$ or $NaBH_4$.

The quantity of reducing agent used can vary widely from the stoichiometric quantity up to an excess representing for example 20 times the stoichiometry.

When a reducing agent is used which leads to the release of a halogenated acid, for example trichlorosilane or hexachlorodisilazane, a base is added, preferably an amine in order to trap the halogenated acid (hydrochloric) released.

As more particular examples, picolines, pyridine, 2-ethylpyridine, 4-ethylpyridine, 2-methylpyridine, 4-methylpyridine, 2,6-methylpyridine, imidazole, 1-methylimidazole, TMEDA (tetraethylenediamine), N-methylpyrrolidine, 4-methylmorpholine, triethylamine, DBU (1,8-diazabicyclo[5.4;0]undecene-7).

The quantity of amine is at least equal to the quantity required to trap the halogenated acid released and more often in excess which can range up to 3 times the stoichiometric quantity.

The reaction is carried out in an organic solvent which solubilizes all the reagents. The solvent can be chosen form the aliphatic, aromatic hydrocarbons halogenated or not.

Among all these solvents, toluene and dichloromethane are preferred.

The concentration of diphosphine in the reaction solvent is preferably between 0.05 and 1 mole/litre and yet more particularly between 0.05 and 0.2 mole/litre.

From a practical point of view, most often, the racemic compound, in the form of oxides, then the reducing agent are added to the mixture of solvents and in the presence of an amine.

The reaction is advantageously carried out between 50° C. and 100° C.

The duration of the reaction is generally situated between 30 minutes and 4 hours.

The racemic mixture is in the organic phase.

Sometimes it is necessary to carry out a basic treatment in the case where the reducing agent is in excess in order to destroy it.

After cooling down, a base is then added, preferably, soda, potash or sodium carbonate until a basic pH (pH of at least 8) is obtained. Preferably, a basic aqueous solution is used, preferably, a soda solution having a concentration from 10% to 30%.

The aqueous and organic phases are separated.

The enantiomers of the diphosphines are recovered in the organic phase which is subjected to the standard treatment described previously, followed by extraction with solvent, washing with salt water and optional drying.

A racemic mixture of the two enantiomers is obtained which can then be separated.

The resolution of the racemic mixture of bis-[1-phospha-2,3-diphenyl-4,5-dimethylnorbornadiene] can be carried out according to the process described in FR No. 94/15757 and PCT/FR95/01716, by reacting the racemic mixture with a palladium and/or platinum complex, as auxiliary chiral thus forming diastereoisomer complexes, then said optically pure complexes are resolved.

A palladium complex can be used. This type of auxiliary chiral is widely described in the literature, in particular by Sei Otsuka et al, in the Journal of the American Chemical Society 93, pp. 4301 (1971).

A platinum complex can also be used and more particularly the work of A. C. Cope {Journal of the American Chemical Society 90, pp. 909 (1968)] can be referred to.

The chiral complex used more particularly corresponds to general formula (VII):

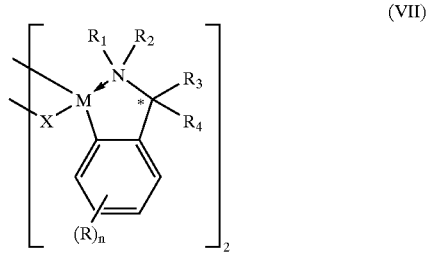

(VII)

in said formula:
M represents palladium and/or platinum,
$R_1$, $R_2$, $R_3$ and $R_4$ represent a hydrogen atom or an alkyl radical having 1 to 10 carbon atoms or a cycloalkyl radical having 3 to 10 carbon atoms,
$R_3$ and $R_4$ are different and at least one of the two represents a hydrogen atom,
R has the meaning given for $R_1$, $R_2$, $R_3$ and $R_4$,
X represents a halogen atom,
n is a number from 0 to 4,
when n is greater than 1, two R radicals and the 2 successive atoms of the benzene ring can form together a ring with 5 to 7 carbon atoms.

More preferably, the complex used corresponds to the aforementioned formula in which $R_1$, $R_2$, $R_3$ and $R_4$ represent a hydrogen atom or a methyl radical. X represents a chlorine atom and n is equal to 0.

When n is equal to 2, the two R radicals form a benzene ring.

As more specific examples of palladium complexes according to the present invention obtained indifferently from (R)-(+) or (S)-(−)-N,N-dimethylphenylethylamine, there can be mentioned:

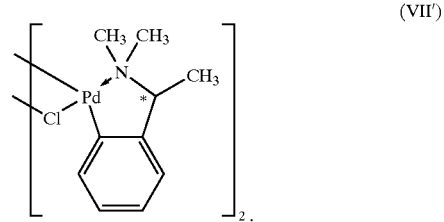

(VII')

The quantity of the aforementioned metal complexes expressed as metal is generally 0.5 to 1 metal atom per phosphorus atom.

An organic solvent is used which solubilizes all the reagents. The solvent must be inert vis-á-vis the diphosphine.

As non-limitative examples of solvents which are suitable for the process according to the invention, there can be mentioned:
the aliphatic hydrocarbons and more particularly the paraffins such as in particular, pentane, hexane, heptane, octane, isooctane, nonane, decane, undecane, tetradecan, petroleum ether and cyclohexane; the aromatic hydrocarbons such as in particular benzene, toluene, the xylenes, ethylbenzene, the diethylbenzenes, the triethylbenzenes, cumene, pseudocumene, the petroleum cuts constituted by a mixture of alkylbenzenes in particular cuts of Solvesso® type.

the aliphatic or aromatic halogenated hydrocarbons, and there can be mentioned: the perchlorinated hydrocarbons such as in particular trichloromethane, tetrachloroethylene; the partially chlorinated hydrocarbons such as dichloromnethane, dichloroethane, tetrachloroethane, trichloroethylene, 1-chlorobutane, 1,2-dichlorobutane, monochlorobenzene, 1,2-dichlorobenzene, 1,3-dichlorobenzene, 1,4-dichlorobenzene or mixtures of different chlorobenzenes.

Among all these solvents, benzene and toluene are preferred.

The concentration of diphosphine in the reaction solvent is preferably between 0.05 and 1 mole/litre and yet more particularly between 0.05 and 0.2 mole/litre.

The separation is advantageously carried out at ambient temperature generally comprised between 15° C. and 25° C.

It preferably takes place under a controlled inert gas atmosphere. A rare gas atmosphere can be established, preferably argon, but it is more economical to use nitrogen.

A mixture of palladium or platinum complexes and the diphosphine corresponding to each enantiomer is obtained.

More particularly they correspond to the following formulae:

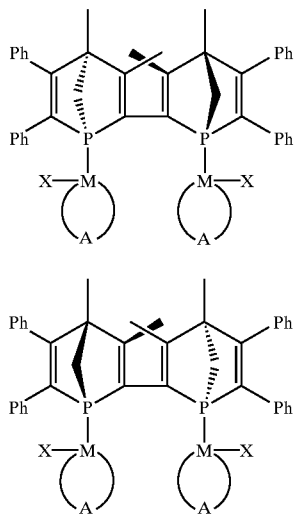

in said formulae, M represents palladium or platinum, X a halogen atom, preferably chlorine and A symbolizes the remainder of a chiral metallic complex corresponding to one of formulae (VII) and preferably (VII').

In a following stage, the two pure enantiomers are recovered.

The solvent is concentrated by evaporation, then the separation is carried out in a known manner [A. Bertheillier—Dunod Paris (1972)] by liquid chromatography on a column, preferably with a silica support.

The column is eluted with a mixture of suitable solvents, preferably, a toluene/ethyl acetate mixture preferably containing 80% by volume of toluene and 20% by volume of ethyl acetate.

The two isolated pure enantiomers are recovered in the form of two diastereoisomer complexes having the following characteristics.

$NMR^{31}P=\delta(CH_2Cl_2)=55.9$ ppm $NMR^{31}P=\delta(CH_2Cl_2)=53.6$ ppm

The two pure enantiomers of the diphosphine are recovered by carrying out the decomplexation.

To this end, a salt of hydrocyanic acid is used, preferably, an alkaline salt and yet more preferably sodium: said salt being solubilized in the minimum quantity of water necessary.

The complexes are solubilized in an organic solvent such as, for example, dichloromethane, then the salt of hydrocyanic acid is introduced under agitation, generally used in an excess representing from 2 to 5 moles per metal atom.

The operation is also carried out under a controlled atmosphere and at ambient temperature.

The enantiomer is recovered in the organic phase which is separated, washed with water and dried, for example, over sodium sulphate.

The two isolated, pure enantiomers of bis-[1-phospha-2,3-diphenyl-4,5-dimethylnorbornadiene] are obtained corresponding to formulae [(Ia)—S,S)(+)] and [(ib)—(R,R)(−)] mentioned previously, the characteristics of which are as follows:

$NMR^{31}P=\delta(CDCl_3)=-13.2$ ppm−$[\alpha]_D=+231°$ (c=1, $C_6D_6$).

$NMR^{31}P=\delta(CDCl_3)=-13.2$ ppm−$[\alpha]_D=+198°$ (c=1, $C_6D_6$).

(with an $[\alpha]_D$ determined for a concentration of 10 mg/ml and at ambient temperature).

Enantiomers Sulphide Route

When the optically active diphosphines are prepared according to a sulphide route, the resolution of the racemic mixture of bis-[1-phosphia-2,3-diphenyl-4.5-dimethylnorbornadiene]disulphide (IX'r) is carried out on a chiral column, which allows the optically active disulphides of bis-[1-phospha-2,3-diphenyl-4,5-dimethylnorbornadiene] (IX'a) and (IX'b) to be obtained, the they are reduced to diphosphines thus leading to the optically active diphosphines (Ia) and (Ib).

The reduction of disulphides to diphosphines is carried out by reaction with a phosphorus containing reagent of $PBu_3$ or $P(CH_2CH_2CN)_3$ type: the reaction being carried out in an organic solvent medium, for example an aromatic hydrocarbon, preferably, toluene.

The reaction is generally carried out at the reflux temperature of the reaction solvent.

In this way, the two enantiomers are obtained:

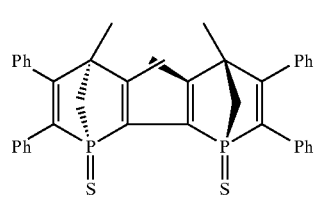

-continued

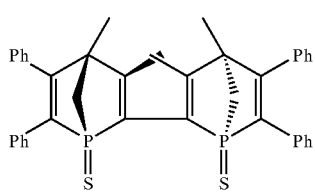

(IX'b)

Another variant consists of reducing the racemic mixtures of the disulphides of bis-[1-phospha-2,3-diphenyl-4,5-dimethylnorbornadiene] (IX'r) to a racemic mixture of bis-[1-phospha-2,3-diphenyl-4,5-dimethylnorbornadiene] (Ir) then carrying out the resolution of the racemic mixture of bis-[1-phospha-2,3-diphenyl-4,5-dimethylnorbornadiene] to optically active phosphines (Ia) and (Ib).

The reduction of the racemic mixture of the disulphides of diphosphines is carried out in the manner mentioned previously for the optically active disulphides of diphosphines.

Finally, another variant of the invention consists of converting the racemic mixture of the disulphides of bis-[1-phospha-2,3-diphenyl-4,5-dimethylnorbornadiene] to a racemic mixture of the dioxides of bis-[1-phospha-2,3-diphenyl-4,5-dimethylnorbornadiene] then the optically active diphosphines (Ia) and (Ib) are obtained according to the routes mentioned above.

It is possible to convert the disulphides of diphosphines to dioxides of diphosphines, by any appropriate means, in particular by reaction of the disulphides of diphosphines with cyclohexene oxide, in trifluoroacetic acid and in an organic solvent medium, in particular in a halogenated aliphatic hydrocarbon, preferably, methylene chloride.

The racemic mixture (IXr) is obtained which is treated as mentioned previously.

The optically active diphosphines obtained according to the process according to the invention has a quite particular use in organic chemistry, in asymmetrical synthesis processes.

The optically active diphosphines according to the invention can be used for the preparation of metallic complexes, allowing the asymmetrical hydrogenation of unsaturated derivatives.

More particularly they can be used to carry out asymmetrical hydrogenation reactions.

The optically active diphosphines according to the invention can be used for the preparation of metallic complexes, allowing the asymmetrical hydrogenation in particular of unsaturated α-β carboxylic acids and/or derivatives and ketonic compounds.

The optically active diphosphines of formula (Ia) and (Ib) serve as ligands in the formation of complex coordinates with transition metals.

As examples of transition metals capable of forming complexes, there can be mentioned in particular metals such as rhodium, ruthenium, rhenium, iridium, cobalt, nickel, platinum, palladium.

Among the aforementioned metals, rhodium, rhenium and iridium are preferred.

Specific examples of said complexes of the present invention are given hereafter, in a non-limitative fashion.

In said formulae, (P*P) represents the diphosphine of formula (Ia) or (Ib).

The complexes of rhodium and iridium can be represented by the following formulae:

(XIVa)

(XIVb)

(P*P) represents in formula (XIVa) the diphosphine of formula (Ia) and in formula (XIVb) the diphosphine of formula (Ib), M represents rhodium or iridium, Y represents an anionic coordination ligand, L represents a neutral ligand.

The preferred complexes of rhodium or iridium correspond to formula (XIVa) or (XIVb) in which:

L represents an olefin having from 2 to 12 carbon atoms and two ligands L can be linked together to form a linear or cyclic, polyunsaturated hydrocarbon chain; L preferably representing 1,5-cyclooctadiene, norbomadiene, ethylene, Y represents a $PF_6^-$, $PCl_6^-$, $BF_4^-$, $BCl_4^-$, $SbF_6^-$, $SbCl_6^-$, $BPh_4^-$, $ClO_4^-$, $CN^-$, $CF_3SO_3^-$ anion, preferably halogen, $CL^-$ or $Br^-$, one of the following anions: 1,3-diketonate, alkylcarboxyiate, haloalkylcarboxyiate, with a lower alkyl radical, a phenylcarboxylate or phenolate anion the benzene ring of which can be substituted by lower alkyl radicals and/or halogen atoms.

By lower alkyl radicals is generally meant a linear or branched alkyl radical having 1 to 4 carbon atoms.

Other iridium complexes can be represented by the formulae:

(XVa)

(XVb)

in said formulae, (P*P), L and Y have the meanings given for formulae (XIVa) and (XIVb).

As regards the ruthenium complexes, they preferably correspond to the following formulae:

(XVIa)

(XVIb)

in said formulae:

(P*P) represents in formula (XVIa) the diphosphine of formula (Ia) and in formula (XVIb) the-diphosphine of formula (Ib), $Y_1$ identical or different, preferably represent, a $PF_6^-$, $PCl_6^-$, $BF_4^-$, $BCl_4^-$, $SbF_6^-$, $SbCl_6^-$, $BPh^-$, $ClO_4^-$, $CF_3SO_3$ anion, a halogen atom, more particularly, chlorine or bromine or a carboxylate anion, preferably, acetate, trifluoroacetate.

Other ruthenium complexes capable of being used in the process according to the invention correspond to the formulae below:

(XVIc)

(XVId)

in said formulae:
(P*P) represents in formula (XVIc) the diphosphine of formula (Ia) and in formula (XVId) the diphosphine of formula (Ib),
Ar represents benzene, p-methylisopropylbenzene, hexamethylbenzene,
$Y_1$, represents a halogen atom, preferably, chlorine or bromine,
$Y_2$ preferably represents, a $PF_6^-$, $PCl_6^-$, $BF_4^-$, $BCl_4^-$, $SbF_6^-$, $SbCl_6^-$, $BPh_4^-$, $ClO_4^-$, $CF_3SO_3^-$ anions.

It is also possible to use complexes based on palladium and platinum in the process according to the invention.

As more specific examples of said complexes, there can be mentioned amongst others $PdCl_2(P*P)$ and $PtCl_2(P*P)$ in which (P*P) represents the diphosphine of formula (Ia) or (Ib).

The complexes containing the aforementioned diphosphine and the transition metal can be prepared according to known techniques described in the literature.

For the preparation of ruthenium complexes, reference can be made to the publication by J-P. Genêt [Acros Organics Acta, 1, No. 1 pp. 1–8 (1994)] and for the other complexes to the article by Schrock R. and Osborn J. A. [Journal of the American Chemical Society, 93, pp. 2397 (1971)].

They can be prepared in particular by the reaction of the diphosphine of formula (Ia) or (Ib) with the transition metal compound in a suitable organic solvent.

The reaction is carried out at a temperature comprised between ambient temperature (from 15 to 25° C.) and the reflux temperature of the reaction solvent.

As examples of organic solvents there can be mentioned amongst others, aliphatic hydrocarbons, halogenated or not, and more particularly hexane, heptane, isooctane, decane, benzene, toluene, methylene chloride, chloroform, solvents of ether or acetone type and in particular diethylether, tetrahydrofuran, acetone, methylethylketone; solvents of alcohol type, preferably, methanol or ethanol.

The metallic complexes according to the invention, recovered according to standard techniques (filtration or crystallization) are used in the asymmetrical hydrogenation reactions of substrates specified in PCT/FR95/01716 and in PCT/FR97/01154.

The αβ-unsaturated carboxylic acid and/or its derivatives more particularly correspond to formula (X):

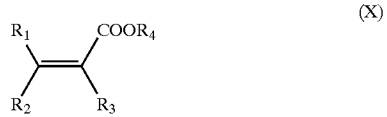

in said formula (X):
$R_1$, $R_2$, $R_3$ and $R_4$ represent a hydrogen atom or any hydrocarbon group, in as much as:
if $R_1$ is different from $R_2$ and different from a hydrogen atom then $R_3$ can be any hydrocarbon or functional group designated by ℜ,
if $R_1$ or $R_2$ represents a hydrogen atom and if $R_1$ is different from $R_2$ then $R_3$ is different from a hydrogen atom and different from —$COOR_4$,
if $R_1$ is identical to $R_2$ and represents any hydrocarbon or functional group designated by ℜ then $R_3$ is different from —CH—(ℜ)$_2$ and different from —$COOR_4$.
one of the $R_1$, $R_2$ and $R_3$ groups can represent a functional group.

The αβ-unsaturated carboxylic acid and/or derivative preferably corresponds to formula (X) in which the identical or different $R_1$ to $R_4$ radicals represent an optionally substituted hydrocarbon radical having 1 to 20 carbon atoms which can be a linear or branched, saturated or unsaturated, acyclic aliphatic radical; a monocyclic or polycyclic, saturated, unsaturated or aromatic, carbocyclic or heterocyclic radical; a linear or branched, saturated or unsaturated, aliphatic radical which carries a cyclic substituent.

As preferred examples of the carboxylic acids used, there can be mentioned a substituted acrylic acid precursor of an amino acid, itaconic acid and/or derivative, arylpropionic acid and/or derivative.

Other substrates which can be hydrogenated are the ketones and derivatives in particular simple ketones, ketones functionalized in α, β, γ, or δ position and derivatives (ketoacids, ketoesters, thioacids, thioesters), diketonic compounds having a carbonyl group in α, β, γ, or δ position with respect to a first carbonyl group.

The following examples, given by way of non-limitative examples, illustrate the present invention.

EXAMPLES

Example 1

Preparation of diphosphine dioxides.

In a 250 ml flask provided with a magnetic stirrer, 4 g (6.92 mmol) of a mixture of diastereoisomers of bis-(1-phospha-2,3 diphenyl-4,5-dimethylnorbornadiene] in meso (Im) and racemic d/l (Ir) form are dissolved in 100 ml of toluene in the respective proportions of 25 (d/l) and 75 (meso).

This mixture is obtained according to the operating method given in the Application PCT/FR95/01716.

The solution obtained is heated to 80° C. and 9 ml of an aqueous solution of hydrogen peroxide at 15% by weight is added.

The agitation and the temperature are maintained for 30 mins.

After cooling down, 100 ml water is added and the two phases are decanted.

The organic phase is washed twice with water, the aqueous phase twice with dichloromethane.

The different organic fractions are combined which are then dried over sodium sulphate.

After evaporation, the residue is subjected to chromatography on silica gel (granulometry 0.060 mm) in order to separate these two products using an eluent.

The meso is recovered first eluting with ethyl acetate.

The racemic is recovered second with a mixture of ethyl acetate /methanol 80/20 by volume.

The two oxides are purified separately by precipitation from ethyl acetate.

2.8 g of meso and 1.2 g of racemic are obtained (94%).

NMR$^{31}$ P=δ(CDCl$_3$)=48.18 ppm—minority isomer corresponding to meso.

NMR$^{31}$ P=δ(CDCl$_3$)=47.77 ppm—majority isomer corresponding to racemic.

Example 2

Reduction of diphosphine dioxides to diphosphines.

In a 100 ml flask provided with a magnetic stirrer, 1 g (1.96 mmol) of the racemic mixture (d/l) obtained according to Example 1 is dissolved, under argon, in 40 ml of a 1,2-dichloroethane/toluene mixture 1/1 by volume, and 2 ml of pyridine is added to the reaction medium.

A solution of 2 ml of HSiCl$_3$ (19.8 mmol, d=1.342) in 2 ml of toluene is then added dropwise over ten minutes and at ambient temperature.

15

The reaction medium is heated at 80° C. for 30 mins.

When the reaction is completed, the medium is cooled down.

An aqueous soda solution at 30% is added until the solution is basic.

The diphosphine (d/l) is extracted in standard manner by decantation, the organic phase is washed with water and the aqueous phase is washed with ether.

The different organic fractions are combined then dried over sodium sulphate.

After evaporation of the solvent, the residue which contains the phosphine is chromatographed rapidly on silica gel eluting with dichloromethane.

The phosphine in the form of a white powder is thus recovered after evaporation of the chromatography solvent.

1.0 g is recovered which corresponds to a yield of 88%.

Example 3

Preparation of diphosphine disulphides.

In a 250 ml flask provided with a magnetic stirrer, 2.9 g (5 mmol) of a mixture of diastereoisomers of bis-[1-phospha-2,3 diphenyl-4,5-dimethylnorbornadiene] in meso (Im) form and racermic d/l (Ir) form is dissolved in 50 ml of toluene in the respective proportions 25(d/l) and 75 (meso).

This mixture is obtained according to the operating method given in the Application PCT/FR95/01716.

The solution obtained is heated at 80° C. for 5 hours.

After evaporation of the toluene, the residue is subjected to chromatography on silica gel in order to separate these two products using an eluent, dichloromethane.

The meso is recovered first.

The racemic is recovered second.

2.2 g of meso (74%) and 0.7 g of racemic (22%) are obtained.

NMR$^{31}$P=δ(CDCl$_3$)=51.6 and 48.18 ppm—J(A-B)=9.7 Hz.

NMR$^{31}$P=δ(CDCl$_3$)=49.6 ppm.

Example 4

Oxidation of diphosphine disulphides to diphosphine dioxides in racemic form (IXr).

0.7 g (1.1 mmol) of diastereoisomer d/l, obtained previously is solubilized under a flow of argon in 10 ml of CH$_2$Cl$_2$, then 0.5 g of CF$_3$COOH (4.4 mmol) and 0.4 g of cyclohexene oxide (4.4 mmol) are added.

The mixture is heated under reflux of the solvent for 30 mins.

The excess acid is neutralized with a solution of sodium carbonate then the aqueous phase is extracted with ether.

The organic phases are collected and dried over anhydrous magnesium sulphate.

The solvent is evaporated off.

The residue is purified by chromatography on silica gel with a mixture of ethyl acetate /methanol (90/10).

The racemic diphosphine dioxide is obtained.

The two enantiomers are then separated after reduction of the racemic diphosphine dioxide according to the same operating method as in Example 2.

What is claimed is:

1. A process for separating the racemic (Ir) and meso (Im) diastereoisomers of bis-[1-phospha-2,3-diphenyl-4,5-dimethylnorbornadiene] from a mixture thereof, wherein Ir and Im correspond to the formulae:

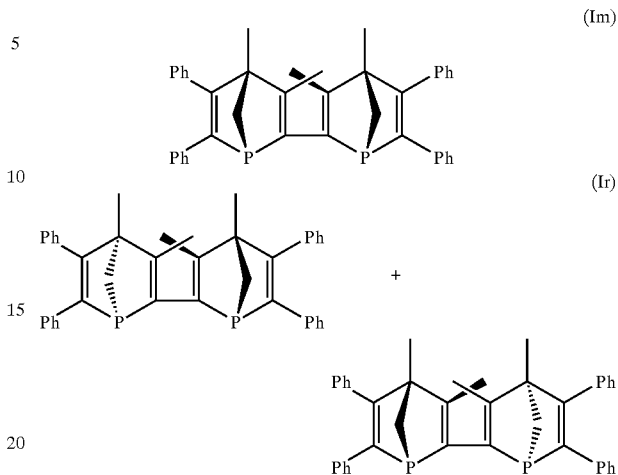

the process comprising converting the mixture of the diastereoisomers of bis-[1-phospha-2,3-diphenyl-4,5-dimethylnorbornadiene] to a mixture of the corresponding diastereoisomers of diphosphine disulphine or dioxide, and then separating the diastereoisomers in dioxide form (IXr and IXm) or disulphide form (IX'r and IX'm), wherein IXr and IXm correspond to the formulae:

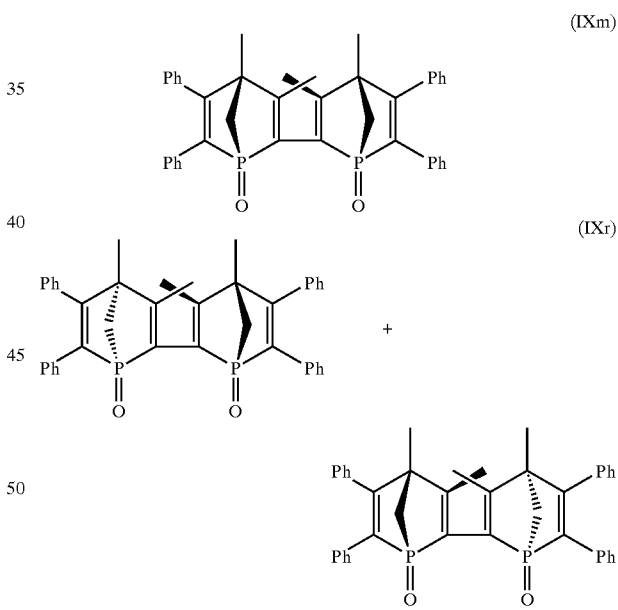

and wherein IX'r and IX'm correspond to the formulae:

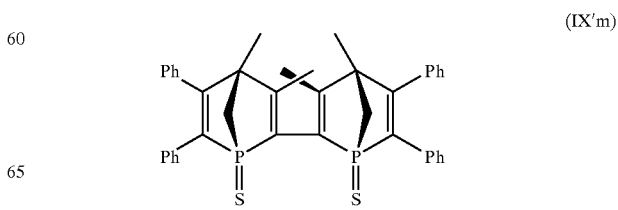

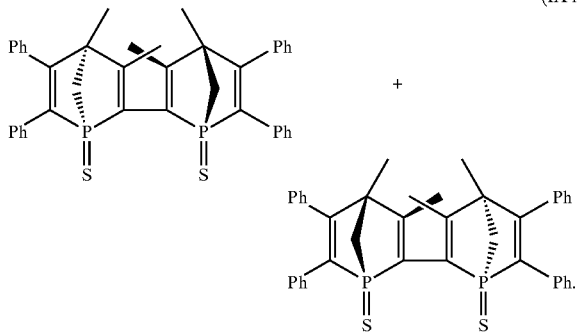

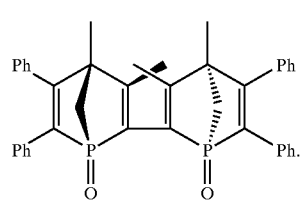

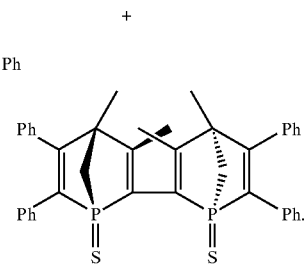

2. The process according to claim 1, wherein the separation of the diastereoisomers of bis-[1-phospha-2,3-diphenyl-4,5-dimethylnorbornadiene]dioxide is conducted by subjecting the mixture of diastereoisomers of bis-[1-phospha-2,3-diphenyl-4,5-dimethylnorbornadiene] to an oxidation reaction thus converting them to bis-[1-phospha-2,3-diphenyl-4,5-dimethylnorbornadiene]dioxide.

3. The process according to claim 2, comprising oxidizing the mixture of diastereoisomers of bis-[1-phospha-2,3-diphenyl-4,5-dimethylnorbomadiene] using an oxidizing agent.

4. The process according to claim 2, wherein the two diastereoisomers (IXm) and (IXr) are separated by liquid chromatography on a column, allowing on the one hand diphosphine dioxide in meso form (IXm) and diphosphine dioxide in racemic form (IXr) to be obtained.

5. A process for the preparation of an optically active diphosphine of formula (Ia) or (Ib):

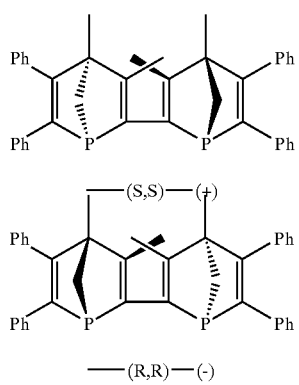

from the diastereoisomer (IXr) obtained according to claim 1, the process comprising:

carrying out the resolution of the diphosphine dioxide (IXr), then separately carrying out the reduction of enantiomers (IXa) or (IXb) of the diphosphine dioxide corresponding to the formulae:

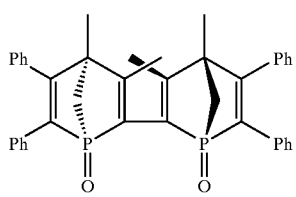

6. The process according to claim 5, wherein the resolution of (IXr) is carried out by chiral liquid chromatography on a chiral chromatography column.

7. A process for preparing an optically active diphosphine of formula (Ia) or (Ib):

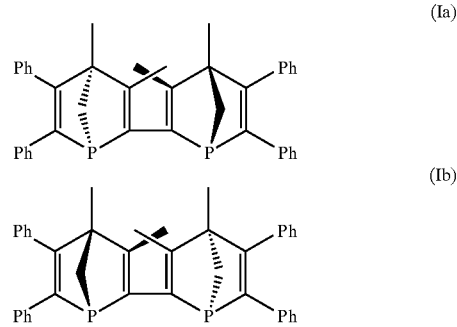

from the diastereoisomer (IXr) obtained according to claim 1, the process comprising:

reducing the diphosphine dioxide (IXr), leading to the diphosphine (Ir); and carrying out the resolution of the diphosphine (Ir).

8. The process according to claim 5, wherein the reduction is carried out with at least one agent selected from the group consisting of trichlorosilane, hexachlorodisilazane, phenyltrisilane, a hydride, and $NaBH_4$.

9. The process according to claim 8, wherein a base is added.

10. The process according to claim 7, comprising carrying out the resolution of the racemic mixture (Ir) of bis-[1-phospha-2,3-diphenyl-4,5-dimethylnorbornadiene] by reacting it with a palladium and/or platinum auxiliary chiral complex in an organic solvent thus forming diastereoisomer complexes, then resolving optically pure complexes.

11. The process according to claim 10, wherein the auxiliary chiral complex corresponds to formula (VII):

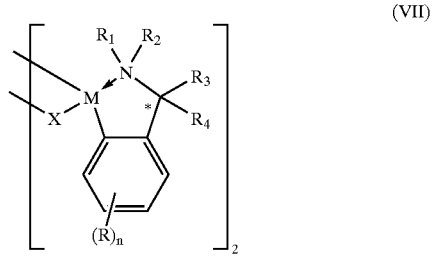

in said formula:
M represents palladium and/or platinum,
$R_1$, $R_2$, $R_3$ and $R_4$ represent a hydrogen atom or an alkyl radical having 1 to 10 carbon atoms or a cycloalkyl radical having 3 to 10 carbon atoms,
$R_3$ and $R_4$ are different and at least one of the two represents a hydrogen atom, R has the meaning given for $R_1$, $R_2$, $R_3$ and $R_4$, X represents a halogen atom, n is a number from 0 to 4, when n is greater than 1, two R radicals and the 2 successive atoms of the benzene ring can form together, a ring having 5 to 7 carbon atoms.

12. The process according to claim 11, wherein the auxiliary chiral complex corresponds to formula (VII) in which $R_1$, $R_2$, $R_3$ and $R_4$ represent a hydrogen atom or a methyl radical, X represents a chlorine atom and n is equal to 0.

13. The process according to claim 11, wherein the auxiliary chiral complex corresponds to formula (VII) in which $R_1$, $R_2$, $R_3$ and $R_4$ represent a hydrogen atom or a methyl radical, X represents a chlorine atom and when n is equal to 2, two R radicals form a benzene ring.

14. The process according to claim 10, wherein the auxiliary chiral corresponds to formula (VII):

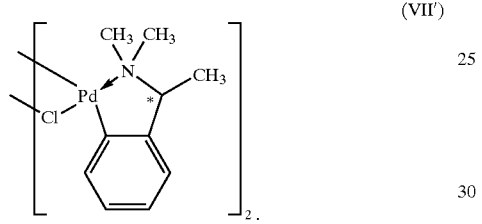

(VII')

15. The process according to claim 10, wherein the separation is carried out by liquid chromatography on a column.

16. The process according to claim 10, wherein the two pure diphosphine enantiomers are recovered by carrying out the solubilization of the complexes in an organic solvent, then decomplexation using a hydrocyanic acid salt.

17. The process according to claim 1, comprising carrying out the separation of the diastereoisomers of bis-[1-phospha-2,3-diphenyl-4,5-dimethylnorbornadiene]disulphide (IX'r and IX'm) obtained by reacting the mixture of diastereoisomers of bis-[1-phospha-2,3diphenyl-4,5-dimethylnorbornadiene] (Ir and Im) with sulphur leading to a mixture of the diastereoisomers of bis-[1-phospha-2,3-diphenyl-4,5-dimethylnorbornadiene]disulphide (IX'r and IX'm).

18. A process for the preparation of an optically active diphosphine of formula (Ia) or (Ib) from a diastereoisomer (IX'r) obtained according to claim 17, the process comprising carrying out the resolution of the racemic mixture of the diphosphine disulphides (IX'r) preferably on a chiral column, and then reducing enantiomers of the disulphides of diphosphines (IX'a) and (IX'b) corresponding to formulae:

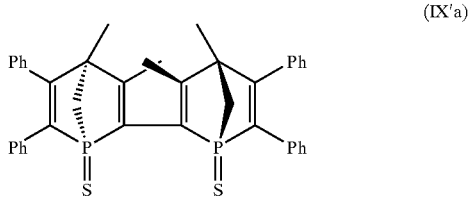

(IX'a)

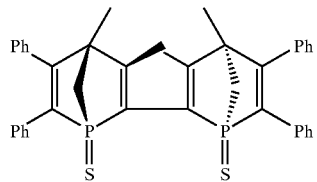

(IX'b)

to enantiomers of diphosphines (Ia) and (Ib) corresponding to formulae:

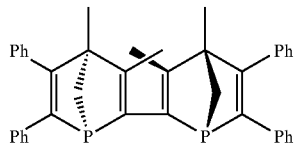

(Ia)

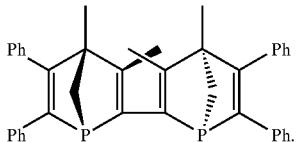

(Ib)

19. A process for the preparation of an optically active diphosphine of formula (1a) or (1b) from the diastereoisomer (IX'r) obtained according to claim 17 comprising reducing the racemic mixture of the disulphides of diphospines (IX'r) to a racemic mixture of diphosphines (Ir) then carrying out the resolution of the racemic mixture of diphosphines to enantiomers (Ia) and (Ib) corresponding to formulae:

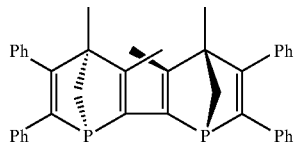

(Ia)

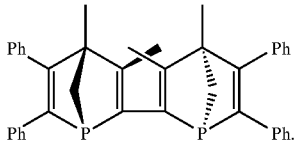

(Ib)

20. The process according to claim 18, wherein the reduction of diphosphine disulphides is carried out by reaction with a phosphorous-containing reagent of $PBu_3$ or $P(CH_2CH_2CN)_3$.

21. A process for preparing an optically active diphosphine of formula (Ia) or (Ib) starting from a diastereoisomer (IX'r) obtained according to claim 17, comprising converting the racemic mixture of disulphides of diphosphines (IX'r) to a racemic mixture of dioxides of diphosphines IXr then obtaining the optically active diphosphines (Ia) and (Ib) corresponding to formulae:

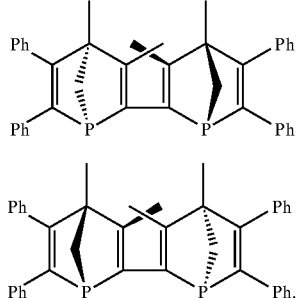

(Ia)

(Ib)

22. The process according to claim 21, wherein the conversion of the diphosphine disulphides to diphosphine dioxides is carried out by reacting the diphosphine disulphides with cyclohexene oxide in trifluoroacetic acid and in an organic solvent medium.

23. Bis-[1-phospha-2,3-diphenyl-4,5-dimethylnorbornadiene]dioxide corresponding to the following formula:

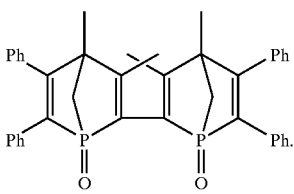

(IX)

24. Diphosphine dioxide of bis-[1-phospha-2,3-diphenyl-4,5-dimethylnorbornadiene] corresponding to the following formulae:

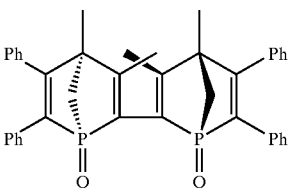

(IXa)

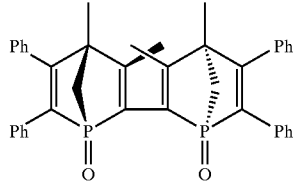

(IXb)

in meso form:

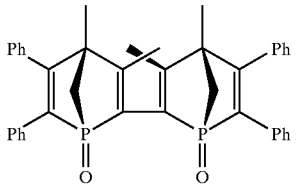

(IXm)

or in racemic form:

(IXr)

25. A method for the preparation of a catalytic metallic complex for selectively carrying out asymmetrical syntheses in organic chemistry, the method comprising reacting the optically active diphosphine (Ia) or (Ib) obtained according to claim 5 with a transition metal in the presence of a solvent.

26. The process according to claim 4 wherein the column has a silica support.

* * * * *